United States Patent [19]

Butland

[11] Patent Number: 4,700,657

[45] Date of Patent: Oct. 20, 1987

[54] FINGERPRINTING SYSTEM INCORPORATING A SPRAY CONTAINER AND A PORTABLE VAPOR TANK

[75] Inventor: Charles L. Butland, Marina del Rey, Calif.

[73] Assignee: Print-Lock Corporation, Playa Del Rey, Calif.

[21] Appl. No.: 754,063

[22] Filed: Jul. 10, 1985

[51] Int. Cl.$^4$ ............................................. B41K 1/00
[52] U.S. Cl. .................................. 118/31.5; 118/719; 118/733; 427/1; 427/145; 427/255.4; 427/345
[58] Field of Search ..................... 118/31.5, 719, 733; 427/1, 145, 255.4, 345

[56] References Cited

U.S. PATENT DOCUMENTS 4,297,383 10/1981 Bourdon ...................... 118/31.5 X Primary Examiner—Janyce A. Bell
Attorney, Agent, or Firm—Mueller and Smith

[57] ABSTRACT

The present invention is a self-contained fingerprinting system which includes a spray container and a portable vapor tank. The spray container discharges into the protable vapor container a mist of atomized particles of cyanoacrylate ester in order to generate vapors thereof. The vapors in the portable vapor tank fume an object suspected of containing latent fingerprints. The portable vapor tank includes a shroud which encloses the vapors from the mist of atomized particles of cyanoacrylate ester, a first supporting member which supports the shroud and a second supporting member which supports the object in front of the spray container. The portable vapor tank also includes a timer which determines the duration of fuming with the vapors and purging apparatus which purges the vapors from the portable vapor tank. The purging apparatus is electrically coupled to the timer and activated thereby at the end of duration of fuming with the vapors. When a fluorescent dye is added to the mist of atomized particles of cyanoacrylate ester in order to generate fluorescent vapors the portable vapor tank further includes an ultraviolet source which exposes latent fingerprints when the ultraviolet light source is shined on the object which contains the latent fingerprints and which has been treated with the fluorescent vapors.

5 Claims, 6 Drawing Figures

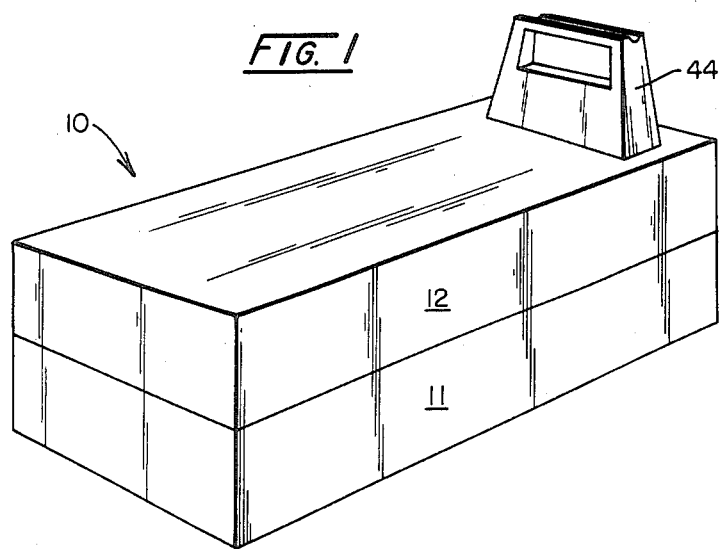
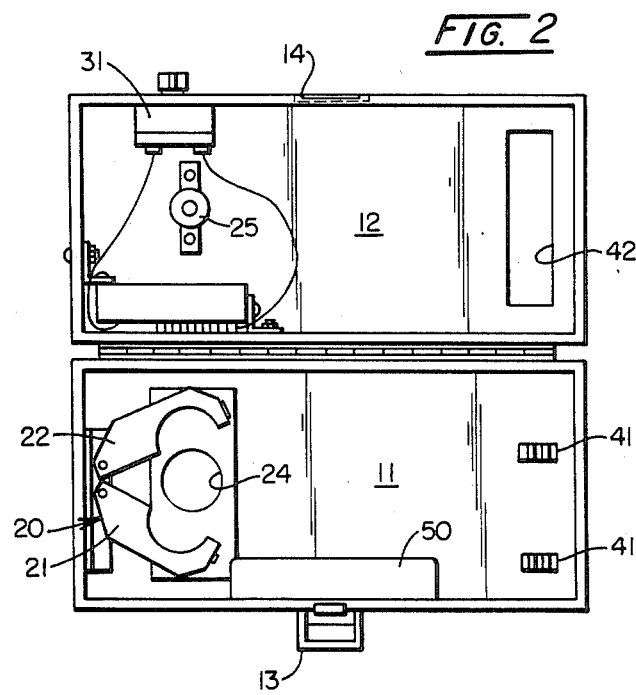

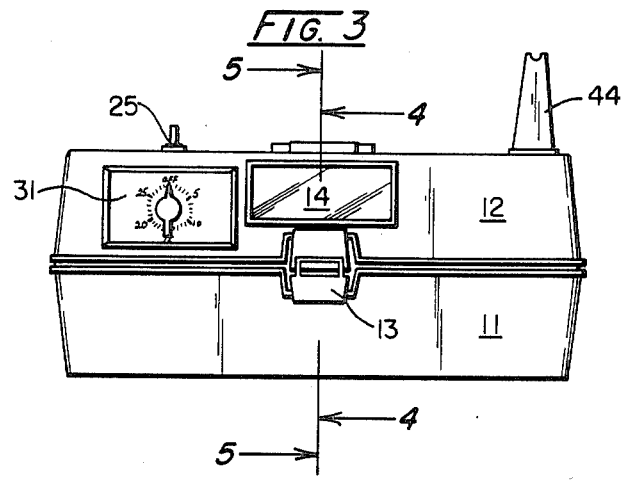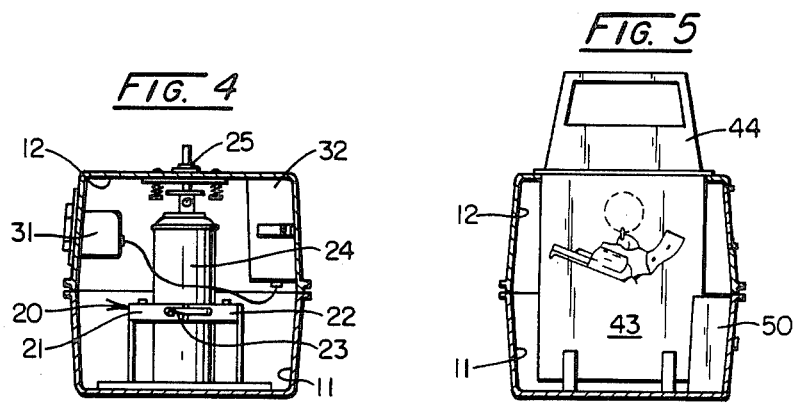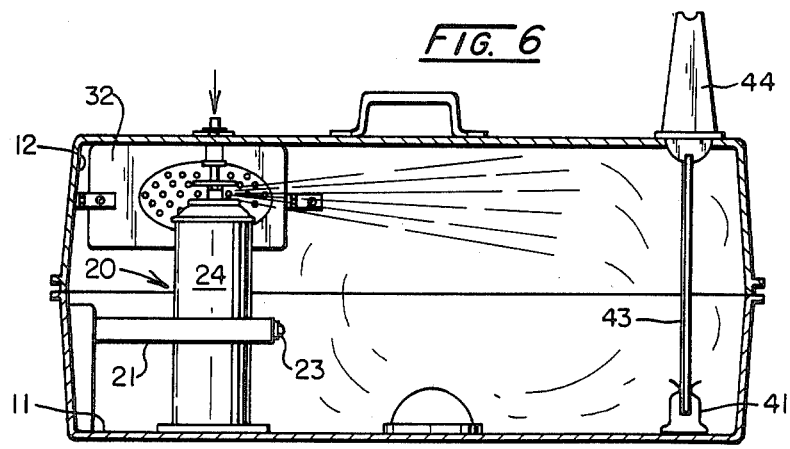

FINGERPRINTING SYSTEM INCORPORATING A SPRAY CONTAINER AND A PORTABLE VAPOR TANK

BACKGROUND OF THE INVENTION

1. Field of the Invention

The present invention relates to a system for fuming an object suspected of containing latent fingerprints thereon with vapors of the chemical cyanoacrylate and more particularly to a portable vapor tank in which the object may be suspended and a spray container which discharges as a fine mist of alkyl-cyanoacrylate ester thereby activating fuming action in the portable vapor tank in order to generate rapid and prolonged fuming of the suspected object with the atomized particles of the alkyl-cyanoacrylate ester.

2. Description of the Prior Art

U.S. Pat. No. 4,297,383, entitled Apparatus and Method for Obtaining Fingerprints, issued to Louis P. Bourdon on Oct. 27, 1981, teaches an apparatus and method for developing latent fingerprints on an object. The apparatus includes a first chamber which contains the object and which closes in order to seal the first chamber air-tight and form a vapor tank and a second chamber which contains a chemical pool and vapors thereof. The apparatus also includes a pump system which pumps vapors from the second chamber into the vapor tank. The method includes the step of pumping the vapors into the vapor tank in order to fume the object with the vapors of the chemical cyanoacrylate and to develop the latent fingerprints on the object being tested inside the vapor tank. U.S. Pat. No. 3,546,003 teaches a similar apparatus and method for obtaining latent fingerprints.

U.S. Pat. No. 4,381,159, entitled Magnetic Fingerprint Dusting Brush, issued to John M. Payne on Apr. 26, 1983, teaches a magnetic fingerprint dusting brush which includes a handle which incorporates a magnetic portion that projects at one end thereof and a non-magnetic shroud which is assembled with the handle closely to shroud the projecting magnetic portion. The shroud includes an inner blind sleeve for closely shrouding the projecting magnetic portion and an outer sleeve to which a cover is detachably secured. The inner blind sleeve has a first portion of greater cross-section for assembly with the handle and a coaxial second portion of lesser cross-section which is connected to the first portion through a shoulder for closely shrouding the projecting magnetic portion. The magnetic fingerprint dusting brush also includes a cover which is detachably securable to the handle and shroud assembly to form in its secured position an enclosed powder reservoir around the shrouded magnetic portion of the handle. The shroud and the cover assembly constitute a powder cartridge with the handle. The powder reservoir contains a mixture of ferrous and dusting powder.

U.S. Pat. No. 4,253,086, entitled Process and Apparatus for Positive Identification of Customers, issued to Szymon Szwarcbier on Feb. 24, 1981, teaches a device for the identification of a person which is based on the use of fingerprints. A master fingerprint of the person appears on a card such as a credit card.

U.S. Pat. No. 4,338,025, entitled Identification Card, Sensor, and System, issued to Elton D. Engel on July 6, 1982, teaches system which identifies either fingerprint or thumbprint pattern of a user to confirm his identity. The system includes an identification card which contains a sliding transparent window which is concealed when the identification card is not in use and a sensor. When the identification card is in use it is inserted into the sensor and the transparent window is slided to a visible position where the user can impress his thumbprint or fingerprint thereon. The sensor scans either his thumbprint or fingeprirnt and tranmits its pattern to a central file for comparision with record thumbprint or fingerprint of the individual who is authorized to use the identification card. An account can be located on the identication card enabling the sensor to scan and transmit to the central file information to identify the record thumbprint or fingerprint against which the user's physical thumbprint or fingerprint is being compared. An authorized user is comfirmed by an appropriate indication at the sensor while an unauthorized user is detected by another appropriate indication.

U.S. Pat. No. 3,947,128, entitled Pattern Comparison, issued to Zvi Weinberger and Avram Kalisky on Mar. 30, 1976, teaches a pattern comparison device which compares patterns of fingerprints thereby making possible the identification of a given person.

U.S. Pat. No. 4,227,631, entitled Valve for a Spray Container, issued to Hilmar Schneider on Oct. 24, 1980, teaches a valve for an aerosol spray container which has a mixing chamber for mixing a gas propellant with an active ingredient in order to produce a finely atomized spray. The gas propellant enters into the valve housing by means of sufficient clearance between the walls of the valve body and the valve housing. The active ingredient and the gas propellant both enter into a mixing chamber through simultaneously openable and closable passage openings. The valve stem of the valve has two channels. One channel in the valve stem provides a flow path for the gas propellant and for the active ingredient mixture, the other channel in the stem providing a flow path substantially for the gas propellant alone. These channels combine in a second mixing chamber resulting in still further atomization of the spray and more efficient utilization of substantially the entire container content. U.S. Pat. No. 3,596,811 teaches a valve for use in connection with an aerosol spray container which holds in its bottom portion a mixture of liquid-gas propellants, an active ingedient and a solvent. The gas propellant is situated above these elements in the remaining free space of the container.

U.S. Pat. No. 4,243,159, entitled Pump Devices for Dispensing Fluids, issued to Walter B. Spatz on Jan. 6, 1981, teaches a spring actuated pump device includes a discharge valve for effecting spraying of a desired quantity of fluid for the spring actuated pump device.

U.S. Pat. No. 4,407,842 entitled Method and Composition Rapidly Developing Latent Fingerprints, issued to Billy H. Shepard on Oct. 4, 1984, teaches a method and composition for developing latent fingerprints on various surfaces including but not limited to glass, plastic, paper and various metals such as copper and brass. A mixture of cyanoacrylate ester, sodium bicarbonate and sulfur produces gaseous fumes to which the latent fingerprints are subjected. Cyanoacrylate ester is a commercially available adhesive sold under either the trademark "Super Glue" or the trademark "Eastman 910." In a very short period of time the gaseous fumes will develop the latent fingerprints so that the fingerprints can be easily lifted by conventional techniques for comparison with known fingerprints. The gaseous fumes are pumped into a portable container under pressure and are stored in the portable, pressurized container which includes a manually operable valve and nozzle arrangement in order to direct the gaseous fumes onto the surfaces which the latent fingerprints may be found.

U.S. Pat. No. 4,461,235, entitled Vapor Phase Activator Pad for a a Self-Contained Fingerprinting Kit, issued to William P. Morton on July 24, 1984, teaches a vapor phase activator pad for use in a self-contained fingerprinting kit which includes a portable vapor tank into which the vapor phase activator pad is placed in order to fume an object suspected of containing latent fingerprints.

U.S. Pat. No. 4,176,205 entitled Fingerprint Powder and Method of Application, issued to Orlando G. Molina on Nov. 27, 1979, teaches a fingerprint powder which includes a powder carrier which is a mixture of silica and talc and a coloring agent which is a fluorescent dye. The fingerprint powder is used to develop latent fingerprints.

U.S. Pat. No. 2,066,535 entitled Finger-Print Detection, issued to Francis F. Lucas on Jan. 5, 1937 also teaches the use of a fluorescent dye for use in developing fingerprints.

SUMMARY OF THE INVENTION

In view of the foregoing factors and conditions which are characteristic of the prior art it is the primary object of the present invention to provide a portable system for rapidly, simply, inexpensively and infallibly identifying a person who wishes to make a credit purchase by means of his identity card such as his credit card or bank card.

It is another object of the present invention to object of the present invention to provide a portable system for fuming an object suspected of containing latent fingerprints thereon with vapors from the mist of atomized particles of cyanoacrylate ester.

It is another object of the present invention to provide a portable vapor tank in which an object may be suspended for use in a system for fuming the object with vapors from the mist of atomized particles of cyanoacrylate ester.

In accordance with the present invention an embodiment of a self-contained fingerprinting system which includes a spray container and a portable vapor tank is described. The spray container discharges into the portable vapor container a mist of atomized particles of cyanoacrylate ester in order to generate vapors thereof. The vapors in the portable vapor tank fume an object suspected of containing latent fingerprints. The portable vapor tank includes a shroud which encloses the vapors from the mist of atomized particles of cyanoacrylate ester, a first supporting member which supports the shroud and a second supporting member which supports the object in front of the spray container. The portable vapor tank also includes a timer which determines the duration of fuming with the vapors and purging apparatus which purges the vapors from the portable vapor tank. The purging apparatus is electrically coupled to the timer and activated thereby at the end of duration of fuming with the vapors. When a fluorescent dye is added to the mist of atomized particles of cyanoacrylate ester in order to generate fluorescent vapors the portable vapor tank further includes a ultraviolet source which exposes latent fingerprints when the ultraviolet light source is shined on the object which contains the latent fingerprints and which has been treated with the fluorescent vapors.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE DRAWING

FIG. 1 is a perspective drawing of a fingerprinting system which has been constructed in accordance with the principles of the present invention and which includes a portable vapor tank and a spray container which is used for fuming an object suspected of containing latent fingerprints thereon with vapors generated from atomized particles of cyanoacrylate ester in the portable vapor tank.

FIG. 2 is a top view of the fingerprinting system of FIG. 1 in which the portable vapor tank is open in order to expose the internal component of the fingerprinting system.

FIG. 3 is a front elevational view of the fingerprinting system of FIG. 1.

FIG. 4 is a side elevation view in cross-section of the fingerprinting system of FIG. 1 taken along the line 4—4 of FIG. 3.

FIG. 5 is a side elevation view in cross-section of the fingerprinting system of FIG. 1 taken along the line 5—5 of FIG. 3.

FIG. 6 is a front elevational view in cross-section of the fingerprinting system of FIG. 1.

DESCRIPTION OF THE PREFERRED EMBODIMENT

In order to best understand the present invention it is necessary to refer to the following description of its preferred embodiment. Referring to FIG. 1 in conjunction with FIG. 2 and FIG. 3 a self-contained fingerprinting system 10 includes a portable vapor tank having a base 11 and top 12 which is hinged to the base 11. In their close position the base 11 and the top 12 are also mechanically coupled by a first latch 13. The top 12 has a viewing window 14.

Referring to FIG. 4 in conjunction with FIG. 2 and FIG. 3 a self-contained fingerprinting system 10 also includes a container holder 20 which has a first arm 21 and a second arm 22 both of which are mechanically hinged to the base 11. A second latch 23 mechanically secures the first and second arms 21 and 22 together. A spray container 24 is placed in a container-holding hole 24a. A push-button is disposed in the top 12 so that it is able to trigger the spray container 24. The spray container 24 discharges into the portable vapor tank 10 a mist of atomized particles of cyanoacrylate ester in order to generate vapors thereof. The vapors in the portable vapor tank fume an object suspected of containing latent fingerprints. The portable vapor tank 10 may include a shroud which is formed out of plastic and which effectively extends the length of the portable vapor tank 10 in order to enclose the vapors from the mist of atomized particles of cyanoacrylate ester. The portable vapor tank 10 also includes a timer 31 which determines the duration of fuming with the vapors and a purging apparatus 32 which purges the vapors from the portable vapor tank 10. The purging apparatus 32 is electrically coupled to the timer and activated thereby at the end of duration of fuming with the vapors. The purging apparatus 32 includes a vacuuming device which has an inlet and an outlet which is fluidly coupled to the inside of the portable vapor tank 10 and a charcoal filter which is fluidly coupled to the inlet of the vacuuming device in order to collect the vapors from the inside of the portable vapor tank 10.

Referring to FIG. 5 in conjunction with FIG. 1, FIG. 2, FIG. 3 and FIG. 6 a self-contained fingerprinting system 10 further includes a supporting apparatus which supports the object in front of the spray container 24. The supporting apparatus includes a pair of stops 41 which are disposed on the base 11 and a rectangular hole in the top which is aligned with the pair of stops 41. The supporting apparatus also includes a slide plate 43 and a stopper 44 which is mechanically coupled to the slide plate 43 and which is to be inserted into the rectangular hole 42 in the top 12.

Referring to FIG. 2 in conjunction with FIG. 3 and FIG. 4 a self-contained fingerprinting system 10 when a fluorescent dye is added to the mist of atomized particles of cyanoacrylate ester in order to generate fluorescent vapors the portable vapor tank 10 further includes a ultraviolet source 50 which exposes latent fingerprints when the ultraviolet light source 50 is shined on the object which contains the latent fingerprints and which has been treated with the fluorescent vapors.

Referring to FIG. 4 in combination with FIG. 6 a spray container 24 includes a container which has a valve with a nozzle. A mixture of a chlorinated organic solvent and a cyanoacrylate ester is disposed in the container. A discharging mechanism discharges a fine mist of atomized particles of the mixture of the chlorinated organic solvent and the cyanoacrylate ester through the nozzle. The mixture of the chlorinated organic solvent and the cyanoacrylate ester includes from 0 percent, but no more than 90 percent, of the chlorinated organic solvent, such as trichoroethane, and at least 1 percent, but as much as 100 percent, of the cyanoacrylate ester. The vapors are generated from the atomized particles of the cyanoacrylate ester in order to fume an object suspected of containing latent fingerprints.

The discharging mechanism is manually operated and may be similar to those discharging mechanisms which U.S. Pat. No. 4,243,159, 4,463,905 and 3,056,560 describe.

U.S. Pat. No. 4,243,159 teaches a spring actuated pump device includes a discharge valve for effecting spraying of a desired quantity of fluid for the spring actuated pump device.

U.S. Pat. No. 3,056,560, entitled Liquid Sprayer, issued to William Martin Vogel, Jr. on Oct. 2, 1962, teaches a liquid sprayer which includes a spray head with one or more apertures or orifices and a cylinder with a piston. The movement of the piston in the cylinder draws the liquid into the spray head. The liquid sprayer atomizes and sprays a liquid through the apertures upon forward movement of the piston. The liquid sprayer is of a general type which U.S. Pat. Nos. 2,194,339, 2,233,161 and 2,178,088 teach.

U.S. Pat. No. 4,227,631 teaches a valve for an aerosol spray container which has a mixing chamber for mixing a gas propellant with an active ingredient in order to produce a finely atomized spray. U.S. Pat. No. 3,596,811 teaches a valve for use in connection with an aerosol spray container which holds in its bottom portion a mixture of liquid-gas propellants, an active ingredient and a solvent.

A fluorescent dye, such a Rhodamine B, may added to the mixture of the chlorinated organic solvent and the alkylcyanoacrylate ester in order to generate fluorescent vapors of the atomized particles of cyanoacrylate ester. Another fluorescent dye, such as Hostasol yellow 8G, which American Hoechst Corporation manufactures, may also be used. An ultraviolet source exposes latent fingerprints when the ultraviolet light source is shined on the object containing the latent fingerprints.

From the foregoing it can be seen that a spray container for use in a system for fuming an object suspected of containing latent fingerprints thereon with vapors generated from atomized particles of cyanoacrylate ester has been described.

Accordingly it is intended that the foregoing disclosure and showing made in the drawing shall be considered only as an illustration of the principles of the present invention.

What is claimed is:

1. A self-contained fingerprinting system comprising: a portable vapor tank in which is disposed a container in which is disposed a mixture of cyanoacrylate ester and a chlorinated organic solvent, a container holder for holding said spray container, supporting means for supporting an object in front of said spray container, and a push-button disposed outside of said vapor tank so that it is able to trigger said spray container, said spray container having discharging means which can be triggered by said push-button to discharge a mist of atomized particles of said cyanoacrylate ester in order to generate vapors thereof in order to fume said object which is suspected of containing latent fingerprints.

2. A self-contained fingerprinting system according to claim 1 wherein said portable vapor tank also comprises:
   a. shrouding means for enclosing said vapors from said mist of atomized particles of cyanoacrylate ester in order to fume with said vapors an object suspected of containing latent fingerprints; and
   b. first supporting means for supporting said shrouding means and said object in front of said discharging means with said supporting means being mechanically coupled to the top of said portable vapor tank.

3. A self-contained fingerprinting system according to claim 1 wherein said portable vapor tank also comprises:
   a. timing means for determining the duration of fuming with said vapors; and
   b. purging means for purging said vapors from said portable vapor tank, said purging means being electrically coupled to said timing means and activated thereby at the end of duration of fuming with said vapors.

4. A self-contained fingerprinting system according to claim 1 wherein a fluorescent dye is added to said mist of atomized particles of cyanoacrylate ester in order to generate fluorescent vapors and wherein said portable vapor tank also comprises a ultraviolet source which exposes latent fingerprints when the ultraviolet light source is shined on the object which contains the latent fingerprints and which has been treated with said fluorescent vapors.

5. A self-contained fingerprinting system according to claim 3 wherein said purging means comprises:
   a. a vacuuming device which has an inlet and an outlet which is fluidly coupled to the inside of said portable vapor tank; and
   b. a charcoal filter which is fluidly coupled to said inlet of said vacuuming device in order to collect said vapors from the inside of said portable vapor tank.

* * * * *